United States Patent [19]

von Alven et al.

[11] Patent Number: 4,762,743
[45] Date of Patent: Aug. 9, 1988

[54] CORRUGATED WEDGE SPACERS FOR SLAB GEL MOLDS

[75] Inventors: Raymond D. von Alven, San Rafael; Craig R. Davis, San Pablo, both of Calif.

[73] Assignee: Bio-Rad Laboratories, Inc., Hercules, Calif.

[21] Appl. No.: 80,042

[22] Filed: Jul. 31, 1987

[51] Int. Cl.⁴ .......... B32B 3/28; G01N 27/26
[52] U.S. Cl. .......... 428/156; 428/167; 428/174; 428/179; 428/182; 204/182.8; 204/299 R
[58] Field of Search .......... 428/156, 167, 174, 176, 428/179, 181, 182, 412; 204/182.8, 182.9, 299 R

[56] References Cited

U.S. PATENT DOCUMENTS

| | | | |
|---|---|---|---|
| 3,091,898 | 6/1963 | Fasold et al. | 428/167 |
| 4,142,960 | 3/1979 | Hahn et al. | 204/182.8 |
| 4,560,459 | 12/1985 | Hoefer | 204/182.8 |
| 4,574,040 | 3/1986 | Delony et al. | 204/182.8 |
| 4,576,693 | 3/1986 | Kreisher et al. | 204/229 R |

Primary Examiner—John E. Kittle
Attorney, Agent, or Firm—Townsend and Townsend

[57] ABSTRACT

Wedge spacers for forming slab gels of increasing cross section are manufactured from strips of thermoplastic material by impressing corrugations into the strips which run lengthwise from one end of each strip to a point along the strip between the two ends. The corrugations decrease in depth from a maximum at the strip end down to flatness at their terminus on the strip face. The forming technique imparts a high degree of reproducibility to the spacers, while still insuring a tight seal.

11 Claims, 2 Drawing Sheets

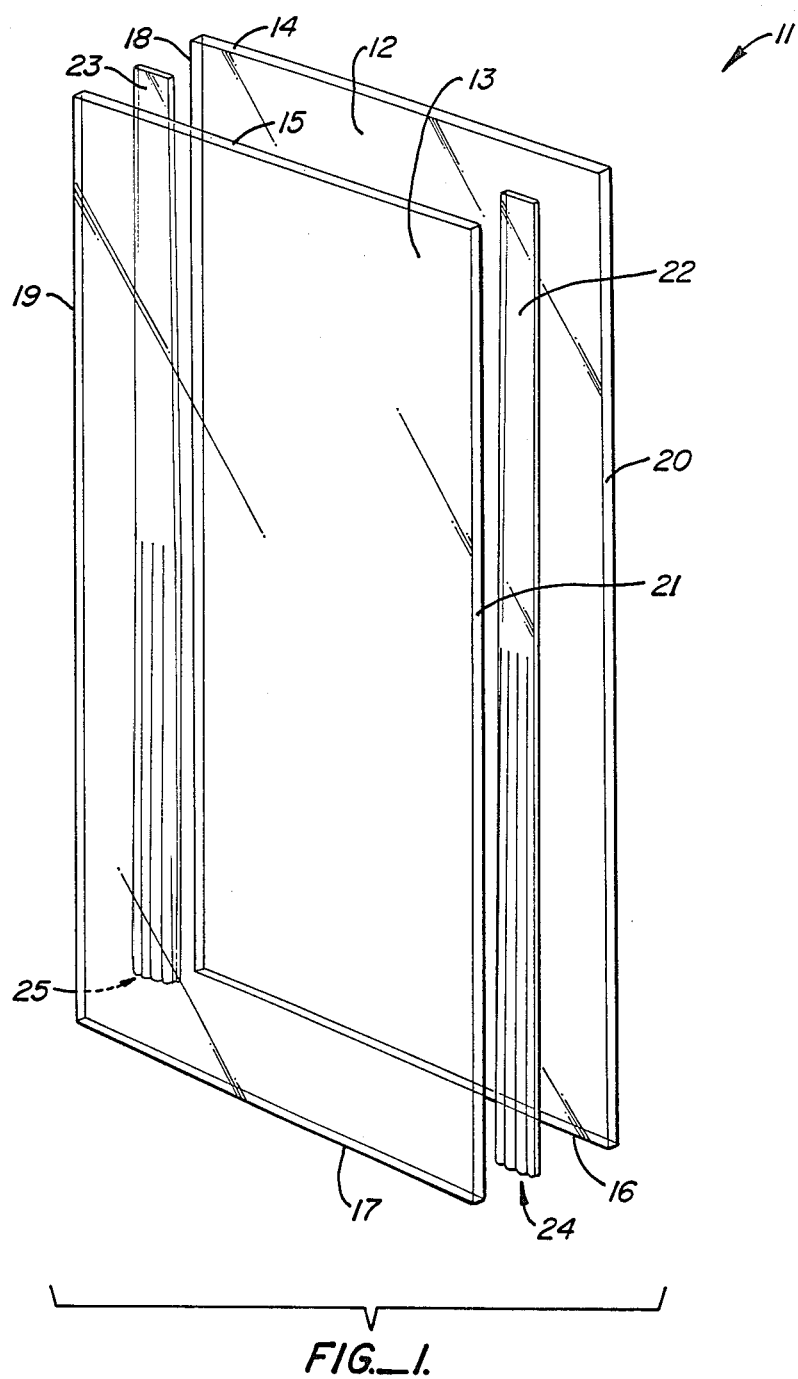
FIG._1.

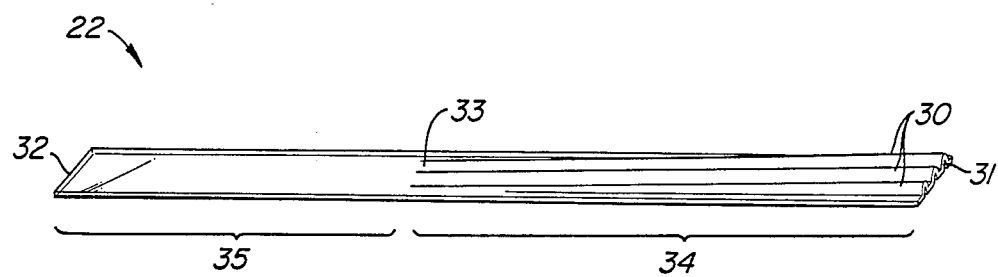
FIG._2.
FIG._3a.
FIG._3b.
FIG._3c.
FIG._3d.
FIG._3e.

CORRUGATED WEDGE SPACERS FOR SLAB GEL MOLDS

BACKGROUND OF THE INVENTION

This invention relates to slab gel electrophoresis, and particularly to molds for slab gels and methods for forming slab gels using such molds.

Slab gels and their use in electrophoresis are widely disclosed in the literature. Recent examples are U.S. Pat. Nos. 4,574,040, issued Mar. 4, 1986 (DeLony et al.) and 4,663,015, issued May 5, 1987 (Sleeter et al.). In systems such as those described in these patents, the gels are formed by pouring a gel-forming liquid into the space between two flat glass plates whose spacing is maintained by spacer strips placed between the plates along two opposing edges, with clamps along each of these edges holding them together like a "sandwich." The spacer strips are smooth so that a seal is formed under the pressure of the clamp, preventing leakage of either the gel-forming solution during gel casting or the buffer solution during electrophoresis.

In gels having a constant thickness and constant gel porosity along the direction of migration, the relationship between the molecular weight of the species being separated and their mobility through the gel is logarithmic. As these species separate into bands and migrate through the gel, the result is a narrow spacing of bands near the starting end of the gel and a relatively wider spacing toward the far end, the end toward which the bands are migrating. This makes detection and analysis difficult in many cases, particularly when many species are to be separated, such as in nucleic acid sequencing.

To counter this effect, gradient gels and wedge-shaped gels have been used in place of the constant gels referred to above. Although gradient gels have been used successfully, they are troublesome to pour, and particularly so in the case of gels of extreme length. Wedge spacers, on the other hand, are easier to use, the thickest end of the spacers being placed at the end away from the starting end of the gel to decrease band mobility. Wedge spacers are difficult to manufacture, however, since they require a high degree of dimensional control for purposes of uniformity and gel reproducibility, as well as a high degree of surface smoothness to prevent leakage. Wedge spacers currently available are machined to their final shape, which makes it difficult to meet these requirements.

SUMMARY OF THE INVENTION

Novel wedge spacer strips have been developed which consist of a strip of sheet material having corrugations along at least a portion of the strip's length, the corrugations being of maximum depth at one end of the strip, and tapering as they proceed inward. The sheet material may be a heat-formable material which permits one to form the corrugations by merely clamping the flat strip against a forming tool by means of an elastomeric pressure pad or an opposing, matching forming tool, and heating to a temperature at which the material of the strip softens to conform to the tool, then permitting the formed strip to cool while still clamped. An indefinite number of identical spacers may be formed in this manner using a single tool. Alternatively, the sheet material may be cold formed. Other methods of manufacture will be readily apparent to those skilled in the art.

Maintenance of the thickness variation of the wedge when in use can be controlled by controlling the stiffness of the corrugated strip. Alternatively, the wedge may be formed to slightly oversized thickness to allow for a slight deformation under the clamping force encountered in the gel sandwich. The smoothness of the strip is maintained during the forming process, ensuring a liquid-tight seal in the gel sandwich.

The corrugated strips of the present invention replace the ground wedge spacer strips of the prior art at a fraction of the cost, while providing a higher degree of product performance.

BRIEF DESCRIPTION OF THE DRAWINGS

FIG. 1 is an exploded perspective view of a gel sandwich using corrugated wedge spacers in accordance with the present invention.

FIG. 2 is a perspective view of one of the corrugated wedge spacers included in the sandwich shown in FIG. 1.

FIGS. 3a, 3b, 3c, 3d, and 3e are end views of corrugated wedge spacers in accordance with the invention, showing several alternative geometries.

DETAILED DESCRIPTION OF THE INVENTION AND PREFERRED EMBODIMENTS

FIG. 1 is offered as an illustration of how corrugated wedge spacers of the present invention might be used in forming the enclosure in which a gel slab is formed. The gel enclosure 11 in this embodiment is formed of two flat glass plates 12, 13, arranged vertically with upper edges 14, 15, lower edges 16, 17, left side edges 18, 19, and right side edges 20, 21. The spacer strips 22, 23 are placed between the two glass plates 12, 13, along the two side edges of each, respectively. Clamps (not shown in this drawing) are placed around the two side edges, compressing the spacer strips between the glass plates to form a liquid-tight seal. An example of such a clamp is shown in U.S. Pat. No. 4,663,015, (Mar. 5, 1987, Sleeter et al.). The disclosure of the latter is incorporated herein by reference.

The spacer strips 22, 23 have tapering corrugations extending from the lower ends 24, 25 to a point approximately midway up along the length of the strips. The effective thickness of the strip is thus greatest at the bottom of the gel enclosure. Under the influence of the clamps, the glass plates 12, 13, will bow slightly to conform to the thickness of the spacer strips 22, 23, thereby giving the space inside a partial wedge-shaped cross section, narrow at the top and wide at the bottom.

The present invention applies to a broad range of geometries. Those shown in the figure are merely illustrative. For example, while the glass plates in the figure are of the same dimensions, glass plates of unequal height may also be used. Either or both of the glass plates may also be replaced by a more complex structure such as a flat elongated reservoir designed to contain a buffer solution, coolant medium or the like. An illustration of the latter is shown in the reference patent identified above.

The enclosure 11 is intended to be open at the top and bottom as shown during use, to permit access by the gel slab retained therein to electrode solutions at each end as needed for electrophoresis to occur. To form the gel solution, the sandwich is assembled with clamps at the side edges and the bottom is sealed, and a gel-forming solution is poured in through the top. A comb-like device is then inserted in the top and left in place while the gel-forming solution polymerizes to form a gel. The comb upon removal then leaves sample-receiving wells along the top edge of the gel. The seal along the bottom of the sandwich is then removed, samples are placed in the wells, and the assembled sandwich is installed in an electrophoresis apparatus in contact with electrode solutions. Electrophoresis then proceeds in the normal manner, with migration of the species in each sample occurring in the downward direction.

A more detailed view of the wedge spacers is seen in FIG. 2. The corrugations 30 extend over a portion of the length of the spacer strip 22, extending from one end 31 lengthwise along the strip, terminating at a point between the two ends 31, 32. In an alternative configuration, the corrugations may extend the entire length of the strip. The corrugations taper along their length, from a maximum depth at the end 31 of the strip, gradually decreasing in depth toward their terminus 33 between the two ends in the embodiment shown in the drawing, or at the opposite end 32 in the alternative configuration. The strip thus contains a corrugated portion 34 and a flat portion 35. The corrugations are at least one in number, preferably at least four, and are parallel to each other and to the longitudinal edges of the strip as shown.

The depth of the corrugations, the degree of taper, and the fractional portion 34 of the strip length which the corrugations occupy may be varied to suit the particular application, reflecting such parameters as the nature and number of species in the sample being separated and the length of the gel. In general, the length of the corrugated portion 34 of the strip will fall within the range of about one-eighth (⅛) of the strip length to the entire strip length, preferably from about one-fourth (¼) to about two-thirds (⅔). Similarly, the ratio of the spacer thickness at the corrugated end 31 to that at the flat end 32 may vary widely, although it will generally be from about 1.5 to about 10, preferably from about 2 to about 5.

The strip itself is preferably a heat-formable material of substantially uniform thickness. Thermoplastic polymers such as polycarbonate are particularly useful. One example is clear Lexan, a product of General Electric Company, Sheet Products Department, Mt. Vernon, Ind., having a thickness of 0.010 inch (0.25 mm). Corrugations may be formed into a strip of such material by compressing the strip against a metal tool, using rubber or some similar material or a matching metal punch which will urge the workpiece against the tool contour when the work piece is softened. Softening is then achieved by heating the workpiece to its softening temperature, which depends on the workpiece composition. For 0.010 inch Lexan, heating to 320° F. (160° C.) in a convection oven will achieve the desired results. The sheet may be supplied with a protective film to prevent scratches during transport and handling. An example of such a film is polyethylene at a thickness of 0.001 inch (0.0025 cm). This film may be left on during the heat forming process to become a protective removable coating on the finished spacer. To prevent damage to the film, however, the working temperature must be reduced to approximately 150° F. to 160° F. (65° C. to 71° C.). As stated above, cold-formable materials may also be used. An example is ABS (acrylonitrile-butadiene-styrene) resin. Certain materials are susceptible to both heat forming and cold forming.

FIGS. 3a through 3e are end views of the strip at the corrugated end 31 (FIG. 2), showing examples of different geometries which may be used for the corrugations. These geometries range from curves to flat surfaces, including combinations thereof. It is important that a continuous sealing surface be provided along the full length of the spacer. Geometries with flat surfaces such as FIGS. 3a, 3d and 3e or large radius curves such as FIG. 3c are preferred for this reason.

The foregoing description is offered primarily for purposes of illustration. It will be readily apparent to those skilled in the art that further variations and modifications of the materials and structures disclosed herein as well as their methods of use may be made without departing from the spirit and scope of the invention.

What is claimed is:

1. A spacer for use between two flat plates when forming a gel slab of graduated thickness therebetween, said spacer comprising a strip of sheet material, having an elongate longitudinal dimension terminating at first and second ends and a relatively narrow transverse dimension, said strip formed to contain at least one corrugation running longitudinally from said first end along at least a portion of the length thereof, said corrugation decreasing in depth from a maximum depth at said first end to define an overall strip thickness greater at said first end than at said second end.

2. A spacer in accordance with claim 1 in which said sheet material is a heat-formable material.

3. A spacer in accordance with claim 1 in which said sheet material is a cold-formable material.

4. A spacer in accordance with claim 1 in which said sheet material is a thermoplastic polymer.

5. A spacer in accordance with claim 1 in which said sheet material is a polycarbonate.

6. A spacer in accordance with claim 1 in which said strip is formed to contain at least four said corrugations.

7. A spacer in accordance with claim 1 in which said overall strip thickness at said first end is from about 1.5 to about 10 times said overall strip thickness at said second end.

8. A spacer in accordance with claim 1 in which said overall strip thickness at said first end is from about 2 to about 5 times said overall strip thickness at said second end.

9. A spacer in accordance with claim 1 in which said corrugations extend along a length ranging from about one-eighth of the length of said strip to the entire length of said strip.

10. A spacer in accordance with claim 1 in which said corrugations extend along about one-fourth to about two-thirds of the length of said strip.

11. A spacer for use between two flat plates when forming a gel slab of graduated thickness therebetween, said spacer comprising a strip of thermoplastic polymer sheet having an elongate longitudinal dimension terminating at first and second ends and a relatively narrow transverse dimension, said strip formed to contain a plurality of corrugations running longitudinally from said first end along about one-fourth to about two-thirds of the length thereof, said corrugations tapering along said longitudinal dimension from a maximum depth at said first end to define an overall strip thickness at said first end which is from about 2 times to about 5 times as great as the thickness of said thermoplastic polymer sheet.

* * * * *